(12) United States Patent
Toupin et al.

(10) Patent No.: US 10,445,473 B2
(45) Date of Patent: Oct. 15, 2019

(54) SYSTEM, METHOD, AND NON-TRANSITORY COMPUTER-READABLE STORAGE MEDIA FOR EVALUATING SEARCH ENGINE RESULTS AND DISPLAYING A VIRTUAL PILL CASE

(71) Applicant: Wal-Mart Stores, Inc., Bentonville, AR (US)

(72) Inventors: Justin Toupin, San Francisco, CA (US); Nathan Thomas Diepenbrock, Highlands Ranch, CO (US)

(73) Assignee: WALMART APOLLO, LLC, Bentonville, AR (US)

( * ) Notice: Subject to any disclaimer, the term of this patent is extended or adjusted under 35 U.S.C. 154(b) by 656 days.

(21) Appl. No.: 15/009,374

(22) Filed: Jan. 28, 2016

(65) Prior Publication Data

US 2017/0220770 A1    Aug. 3, 2017

(51) Int. Cl.
   *G06F 19/00*    (2018.01)
   *G06F 17/30*    (2006.01)
   *G06F 16/951*   (2019.01)

(52) U.S. Cl.
   CPC ........ *G06F 19/3475* (2013.01); *G06F 16/951* (2019.01)

(58) Field of Classification Search
   CPC .. G06F 19/00; G06F 19/3456; G06F 19/3418; G06F 19/3462; G06F 19/3475;

(Continued)

(56) References Cited

U.S. PATENT DOCUMENTS 6,543,683 B2    4/2003  Hoffman
6,711,460 B1    3/2004  Reese (Continued)

FOREIGN PATENT DOCUMENTS

WO    2000075834 A2    12/2000
WO    2007134378 A1    11/2007
WO    2012064026 A2    5/2012

OTHER PUBLICATIONS

Website: www.blueapron.com—Blue Apron: Fresh Ingredients, Original Recipes, Delivered to You; downloaded Feb. 3, 2016; 29 pages total.

*Primary Examiner* — Maroun P Kanaan
(74) *Attorney, Agent, or Firm* — Bryan Cave Leighton Paisner LLP

(57) ABSTRACT

Systems, methods, and computer-readable storage media that assist pharmacy customers with medication adherence are disclosed. A user interface on a user device includes a virtual pill case including prescription information about a medication. A processing device includes a pharmacy account module, a search engine module, and a communications module. The pharmacy account module receives a request to monitor a user activity, stores the request in a database, and initiates a data search operation, and transmits prescription information to the search engine module. The search engine module receives the prescription information, generates a search on a third party server, and receives and sends the results to the pharmacy account module. The pharmacy account module evaluates the results to retrieve updated medication information and updates the virtual pill case, determines a triggering event associated with the medication occurred, and generates a notification. The communications module transmits the notification to the user.

21 Claims, 15 Drawing Sheets

(58) Field of Classification Search
CPC .. G06F 19/3481; G06F 19/321; G06F 19/325; G06F 19/328; G06F 19/36; G06F 19/324; G06F 19/326; G16H 10/60; G16H 20/13; G16H 50/20; G16H 20/10; G16H 40/63; G16H 70/40; G06Q 50/24
See application file for complete search history.

(56) References Cited

U.S. PATENT DOCUMENTS

| | | | |
|---|---|---|---|
| 6,898,598 B2 | 5/2005 | Himmel et al. | |
| 7,487,912 B2 | 2/2009 | Seifert et al. | |
| 7,747,695 B1* | 6/2010 | Morris | G06F 9/542 |
| | | | 705/5 |
| 8,606,698 B2 | 12/2013 | Schultz et al. | |
| 9,043,217 B2 | 5/2015 | Cashman et al. | |
| 9,195,959 B1 | 11/2015 | Lopez et al. | |
| 9,607,345 B1 | 3/2017 | Hendren et al. | |
| 2002/0073043 A1 | 6/2002 | Herman et al. | |
| 2003/0096616 A1 | 5/2003 | Speight et al. | |
| 2003/0120607 A1 | 6/2003 | Piotrowski | |
| 2003/0187672 A1 | 10/2003 | Gibson | |
| 2003/0216950 A1 | 11/2003 | Chen | |
| 2004/0204954 A1 | 10/2004 | Lacko | |
| 2004/0236635 A1 | 11/2004 | Publicover | |
| 2005/0165651 A1 | 7/2005 | Mohan | |
| 2007/0088624 A1 | 4/2007 | Vaughn et al. | |
| 2007/0124170 A1 | 5/2007 | Cabell et al. | |
| 2007/0150375 A1 | 6/2007 | Yang | |
| 2007/0204169 A1 | 8/2007 | Bahl et al. | |
| 2007/0226071 A1 | 9/2007 | Kern et al. | |
| 2008/0133283 A1 | 6/2008 | Backer et al. | |
| 2009/0076875 A1 | 3/2009 | Lert, Jr. et al. | |
| 2009/0181131 A1 | 7/2009 | Forbes-Roberts | |
| 2009/0271265 A1 | 10/2009 | Lay et al. | |
| 2010/0121807 A1 | 5/2010 | Perrier et al. | |
| 2011/0016007 A1 | 1/2011 | Shiftan et al. | |
| 2011/0125519 A1 | 5/2011 | Dhoble | |
| 2011/0231272 A1 | 9/2011 | Englund et al. | |
| 2011/0307265 A1 | 12/2011 | Bannis | |
| 2011/0307547 A1 | 12/2011 | Backer et al. | |
| 2011/0313790 A1 | 12/2011 | Yao | |
| 2011/0321127 A1 | 12/2011 | Pitroda et al. | |
| 2012/0072311 A1 | 3/2012 | Khan | |
| 2012/0078673 A1 | 3/2012 | Koke et al. | |
| 2012/0084391 A1 | 4/2012 | Patel et al. | |
| 2012/0114116 A1 | 5/2012 | Sulaiman et al. | |
| 2012/0123674 A1 | 5/2012 | Perks et al. | |
| 2012/0166298 A1 | 6/2012 | Smith et al. | |
| 2012/0191573 A1 | 7/2012 | Miller | |
| 2012/0221446 A1 | 8/2012 | Grigg et al. | |
| 2012/0290609 A1 | 11/2012 | Britt | |
| 2013/0159858 A1 | 6/2013 | Joffray et al. | |
| 2013/0173403 A1 | 7/2013 | Grigg et al. | |
| 2013/0179180 A1 | 7/2013 | Patra | |
| 2013/0196297 A1 | 8/2013 | Anwar | |
| 2013/0224694 A1 | 8/2013 | Moore et al. | |
| 2013/0262155 A1* | 10/2013 | Hinkamp | G06Q 40/08 |
| | | | 705/4 |
| 2013/0290145 A1 | 10/2013 | Durst, Jr. | |
| 2014/0080102 A1 | 3/2014 | Krishna | |
| 2014/0156297 A1 | 6/2014 | Schaefer et al. | |
| 2014/0188648 A1 | 7/2014 | Argue et al. | |
| 2014/0222482 A1 | 8/2014 | Gautam et al. | |
| 2014/0244296 A1 | 8/2014 | Linn et al. | |
| 2014/0258022 A1 | 9/2014 | Zamer et al. | |
| 2014/0279269 A1 | 9/2014 | Brantley et al. | |
| 2015/0161353 A1* | 6/2015 | Emerson | G06F 19/00 |
| | | | 705/2 |
| 2015/0242592 A1 | 8/2015 | Weiss et al. | |
| 2015/0261934 A1 | 9/2015 | Miller | |
| 2015/0285775 A1 | 10/2015 | Gurumohan et al. | |
| 2015/0294084 A1 | 10/2015 | McCauley et al. | |
| 2015/0294387 A1 | 10/2015 | Karmazyn et al. | |
| 2016/0205180 A1 | 7/2016 | Jan et al. | |
| 2016/0364547 A1 | 12/2016 | Love et al. | |
| 2017/0213271 A1 | 7/2017 | Nelms et al. | |
| 2017/0220649 A1 | 8/2017 | Toupin | |
| 2017/0220684 A1 | 8/2017 | Toupin et al. | |
| 2017/0220741 A1 | 8/2017 | Toupin et al. | |
| 2017/0220761 A1 | 8/2017 | Toupin et al. | |
| 2017/0220762 A1 | 8/2017 | Toupin et al. | |
| 2017/0220763 A1 | 8/2017 | Toupin et al. | |
| 2017/0220764 A1 | 8/2017 | Toupin et al. | |
| 2017/0220765 A1 | 8/2017 | Toupin et al. | |
| 2017/0220771 A1 | 8/2017 | Toupin et al. | |
| 2017/0221123 A1 | 8/2017 | Toupin | |
| 2017/0221129 A1 | 8/2017 | Toupin | |
| 2017/0242976 A1 | 8/2017 | Howieson et al. | |
| 2018/0130548 A1 | 5/2018 | Fisher | |

* cited by examiner

| User ID | Drug ID | Prescription Drug | Category | Dosage | No. of Refills |
|---|---|---|---|---|---|
| Alice011 | Drug001 | Albuterol | Bronchodilator | 200 mcg | 2 |
| | Drug005 | Benadryl | Antihistamines | 25mg | 12 |
| Barbara003 | Drug012 | Captopril | Ace Inhibitor | 12.5mg | 5 |
| Carl004 | Drug020 | Digoxin | Glycosides | 750 mcg | 2 |

FIG. 4

SYSTEM, METHOD, AND NON-TRANSITORY COMPUTER-READABLE STORAGE MEDIA FOR EVALUATING SEARCH ENGINE RESULTS AND DISPLAYING A VIRTUAL PILL CASE

COPYRIGHT NOTICE

The figures included herein contain material that is subject to copyright protection. The copyright owner has no objection to the facsimile reproduction by anyone of this patent document as it appears in the U.S. Patent and Trademark Office, patent file or records, but reserves all copyrights whatsoever in the subject matter presented herein.

FIELD OF THE DISCLOSURE

The present invention relates to providing product information to a consumer, and more particularly, to systems, methods, and computer-readable storage media that assist pharmacy customers with medication adherence and generate and display alerts regarding upcoming or missed medication doses to pharmacy customers. The suggested class/subclass of the disclosure is: CLASS 707: DATA PROCESSING: DATABASE AND FILE MANAGEMENT OR DATA STRUCTURES. The suggested Art Unit is 2161.

BACKGROUND

Many pharmacy consumers are prescribed multiple medications to take daily, particularly those who are elderly and/or those suffering from chronic medical conditions. Such consumers often have problems adhering to a medication schedule. Non-adherence to a medication schedule may have a variety of causes, including the patient forgetting to take a dose, failing to timely refill a prescription, or misunderstanding dosing instructions. Failure to adhere to a medication schedule as prescribed results in missed doses of medication(s), resulting in lower efficacy or inefficacy of medications, which may cause adverse health effects and even death. In addition, medication non-adherence may lead to increased health care costs over time.

Many pharmacy consumers desire to obtain information related to the pharmaceutical medications being prescribed to them remotely, e.g., on-line, through the Internet, or using a specially designed application or app on a personal computer or mobile device, such as a tablet or cell phone. At least some known web hosting systems include information associated with pharmaceutical drugs including treated illnesses and potential side effects. However, many of the systems do not address medication adherence issues, nor do they provide personalized information about prescribed medications.

The present invention is aimed at one or more of the problems identified above.

SUMMARY OF THE INVENTION

In different embodiments of the present invention, systems, methods, and computer-readable storage media for generating and displaying information to users via mobile computing devices.

In one embodiment of the present invention, a system for assisting pharmacy customers with medication adherence and generating alerts regarding upcoming or missed medication doses to pharmacy customers is disclosed. A user interface on a user device is accessible to a user and includes a virtual pill case including prescription information about a medication. A processing device in communication with the user interface includes a pharmacy account module, a search engine module, and a communications module. The pharmacy account module receives a request to initiate a notification operation to monitor an activity of the user corresponding to the use of the medication, stores the notification operation request in a database, and initiates a data search operation including transmitting the prescription information to a search engine module. The search engine module receives the prescription information, generates a search on a third party server, receives search results associated with the prescription information from the third party server, and sends the search results to the pharmacy account module. The pharmacy account module further receives the search results from the search engine module, evaluates the search results to retrieve updated information associated with the at least one medication, updates the medication in the virtual pill case with the updated information, determines that a triggering event has occurred, wherein the triggering event is associated with the medication, and generates a notification regarding the triggering event. A communications module transmits the notification to the user.

In another embodiment of the present invention, a method for assisting pharmacy customers with medication adherence and generating alerts regarding upcoming or missed medication doses to pharmacy customers is disclosed. In a first step, a pharmacy account module of a server receives a request to initiate a notification operation to monitor an activity of a user, the activity corresponding to the use of the at least one medication. In a second step, the notification operation request is stored in a database on the server. In a third step, the pharmacy account module initiates a data search operation including transmitting the prescription information to a search engine module. In a fourth step, the search engine module receives the prescription information. In a fifth step, the search engine module generates a search on a third party server. In a sixth step, the search engine module receives search results associated with the prescription information from the third party server. In a seventh step, the search engine module sends the search results to the pharmacy account module. In an eighth step, the pharmacy account module receives the search results. In a ninth step, the pharmacy account module evaluates the search results to retrieve updated information associated with the at least one medication. In a tenth step, the pharmacy account module updates the at least one medication in the virtual pill case with the updated information. In an eleventh step, the pharmacy account module determines that a triggering event has occurred, wherein the triggering event is associated with the at least one medication. In a twelfth step, the pharmacy account module generates a notification regarding the triggering event. In a thirteenth step, a communications module transmits the notification to the user.

In yet another embodiment of the present invention, a computer-readable storage medium for assisting pharmacy customers with medication adherence and generating alerts regarding upcoming or missed medication doses to pharmacy customers is disclosed. A computer readable program is recorded on the non-transitory information recording medium that causes a computer to function as a system. A user interface on a user device is accessible to a user and includes a virtual pill case including prescription information about a medication. A processing device in communication with the user interface includes a pharmacy account module, a search engine module, and a communications module. The pharmacy account module receives a request to initiate a notification operation to monitor an activity of the user corresponding to the use of the medication, stores the notification operation request in a database, and initiates a data search operation including transmitting the prescription information to a search engine module. The search engine module receives the prescription information, generates a search on a third party server, receives search results associated with the prescription information from the third party server, and sends the search results to the pharmacy account module. The pharmacy account module further receives the search results from the search engine module, evaluates the search results to retrieve updated information associated with the at least one medication, updates the medication in the virtual pill case with the updated information, determines that a triggering event has occurred, wherein the triggering event is associated with the medication, and generates a notification regarding the triggering event. A communications module transmits the notification to the user.

BRIEF DESCRIPTION OF THE FIGURES

Non-limiting and non-exhaustive embodiments of the present invention are described with reference to the following figures. Other advantages of the present disclosure will be readily appreciated, as the same becomes better understood by reference to the following detailed description when considered in connection with the accompanying drawings wherein:

FIG. 4 is an illustration of exemplary database records generated by the system of FIG. 1, according to embodiments of the present invention;

Figure 1:
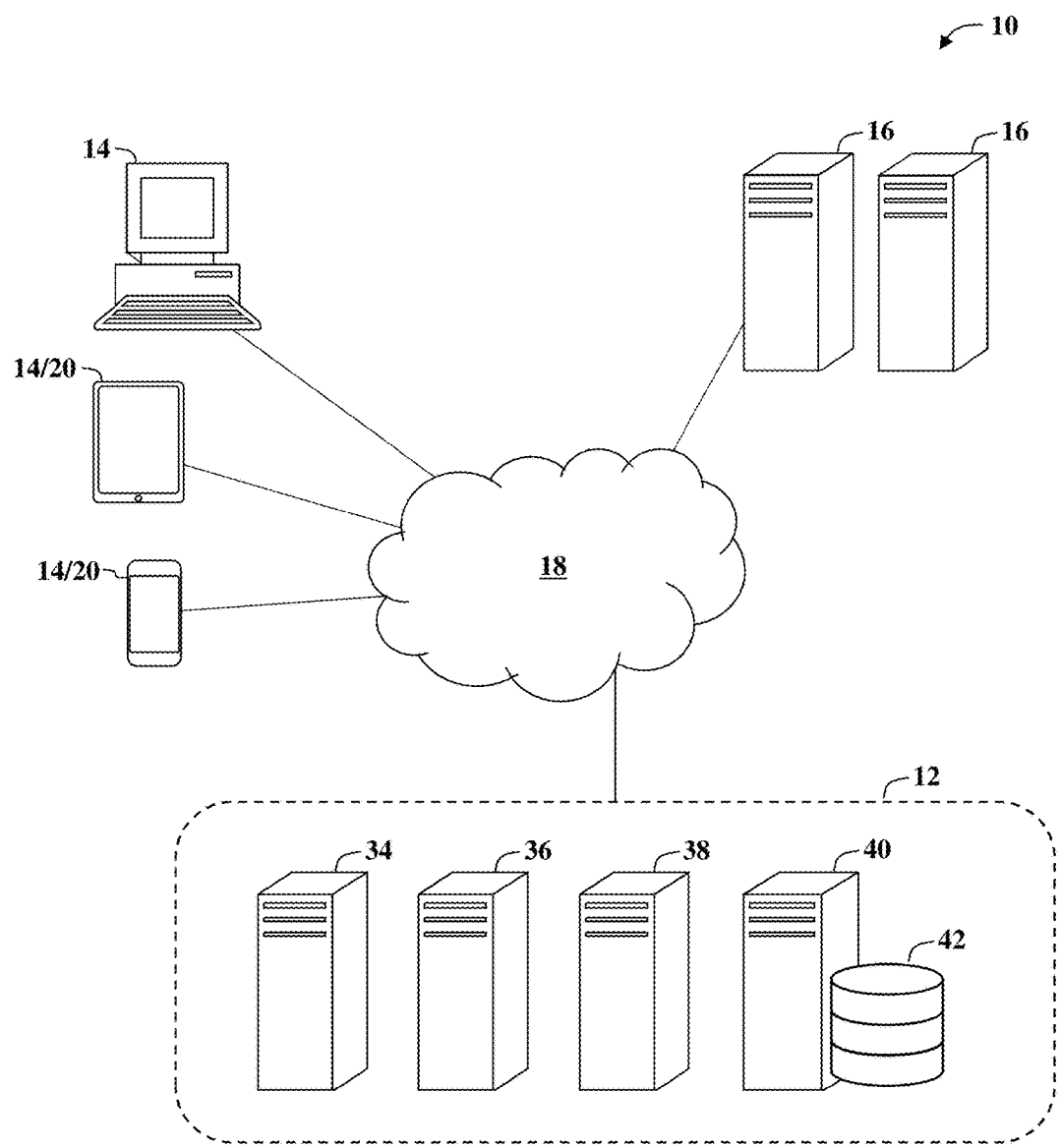
FIG. 1 is a schematic illustrating various aspects of a system, according to the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible media of expression having computer-usable program code embodied in the media.

Any combination of one or more computer-usable or computer-readable media (or medium) may be utilized. For example, a computer-readable media may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable media that can direct a computer or other programmable data processing apparatus to function in a particular manner, such that the instructions stored in the computer-readable media produce an article of manufacture including instruction means which implement the function/act specified in the flowchart and/or block diagram block or blocks.

Several (or different) elements discussed below, and/or claimed, are described as being "coupled", "in communication with", or "configured to be in communication with". This terminology is intended to be non-limiting, and where appropriate, be interpreted to include without limitation, wired and wireless communication using any one or a plurality of a suitable protocols, as well as communication methods that are constantly maintained, are made on a periodic basis, and/or made or initiated on an as needed basis. The term "coupled" means any suitable communications link, including but not limited to the Internet, a LAN, a cellular network, or any suitable communications link. The communications link may include one or more of a wired and wireless connection and may be always connected, connected on a periodic basis, and/or connected on an as needed basis.

With reference to the FIGS. and in operation, the present invention provides a networked computer system 10, methods and computer product media that monitors the activities of pharmacy customers and provides notification of potential drug interactions to a user via a website. Referring to FIG. 1, an exemplary environment in which the networked computer system 10 operates is illustrated. In general, the present invention describes a networked computer system 10 that assists pharmacy customers adhere to a medication schedule and alerts the pharmacy customers about upcoming or missed doses based on the medication schedule. Moreover, the networked computer system 10 is configured to communicate with a mobile device associated with the customer to provide push notifications to the mobile devices including messages about missed or upcoming doses to the pharmacy customers. The system 10 may also include a mobile computer application being stored on a mobile device associated with the pharmacy customer.

The system 10 is configured to generate and store user pharmacy data records associated with pharmacy customers that includes information associated with pharmaceutical drugs being used by the customers. In addition, the user pharmacy data records may include triggering events that are detected by the system. The triggering events may include detecting a date and/or time that a customer is due for a medication dose, or determining that a new or updated prescription is available.

By generating triggering events that trigger corresponding system actions, the system 10 improves the speed and functionality of known computing systems by reducing the amount of computing time required to monitor customer activity, thus reducing the computing resources required to generate and display relevant pharmacy messages to pharmacy customers.

For clarity in discussing the various functions of the system 10, multiple computers and/or servers are discussed as performing different functions. These different computers (or servers) may, however, be implemented in multiple different ways such as modules within a single computer, as nodes of a computer system, etc . . . . The functions performed by the system 10 (or nodes or modules) may be centralized or distributed in any suitable manner across the system 10 and its components, regardless of the location of specific hardware. Furthermore, specific components of the system 10 may be referenced using functional terminology in their names. The function terminology is used solely for purposes of naming convention and to distinguish one element from another in the following discussion. Unless otherwise specified, the name of an element conveys no specific functionality to the element or component.

In the illustrated embodiment, the system 10 includes a server system 12 that is coupled in communication with one or more user computing devices 14 and one or more third party computer servers 16 via a communications network 18. The communications network 18 may be any suitable connection, including the Internet, file transfer protocol (FTP), an Intranet, LAN, a virtual private network (VPN), cellular networks, etc . . . , and may utilize any suitable or combination of technologies including, but not limited to wired and wireless connections, always on connections, connections made periodically, and connections made as needed.

The user computing device 14 may include any suitable device that enables a user to access and communicate with the system 10 including sending and/or receiving information to and from the system 10 and displaying information received from the system 10 to a user. For example, in one embodiment, the user computing device 14 may include, but is not limited to, a desktop computer, a laptop or notebook computer, a tablet computer, smartphone/tablet computer hybrid, a personal data assistant, a handheld mobile device including a cellular telephone, and the like. The user computing device 14, as well as any other connected computer systems and their components included in the system 10, can create message related data and exchange message related data (e.g., near field communication ("NFC") payloads, Bluetooth packets, Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), etc.) over the network.

Figure 2:
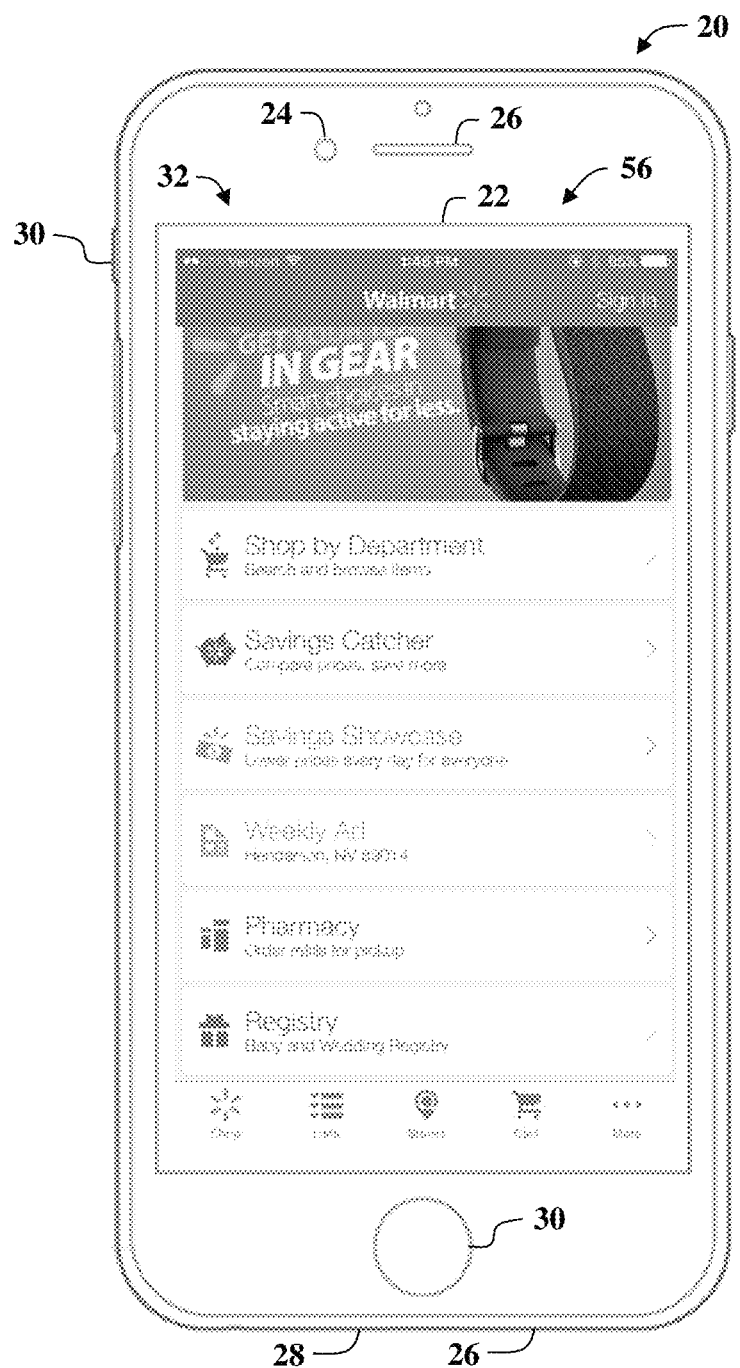
FIG. 2 is a schematic illustrating an exemplary mobile device used with the system of FIG. 1, according to an embodiment of the present invention.

Referring now to FIG. 2, in one embodiment, the user computing device includes a mobile computing device 20 such as, for example, a smartphone such as an iPhone™. The mobile computing device 20 includes a processor coupled to a memory device, and a database for storing various programs and data for use in operating the mobile computing device 20. The mobile computing device 20 may also include a touchscreen display device 22, one or more video image cameras 24, one or more speakers 26, a microphone 28, at least one input button 30, and one or more sensors including, but not limited to, a touch ID fingerprint sensor coupled to an input button 30, a barometer, a three-axis gyro, an accelerometer, proximity sensor, and an ambient light sensor. In addition, the mobile computing device 20 may also include a Wi-Fi antenna, a cellular network antenna, a Bluetooth™ communications device, assisted GPS and GLONASS, a digital compass, and an iBeacon microlocation device.

In the illustrated embodiment, the mobile computing device 20 includes a web browser program stored in the memory device. The processor executes the web browser program to display web pages on the touchscreen display device 22 that includes information received from the server system 12 to enable a user to interact with and operate the server system 12. In addition, the mobile computing device 20 may be programmed to store and execute a mobile program application, e.g. a mobile application, that displays a user interface 32 on the touchscreen display device 22 that allows the user to access the server system 12 to retrieve and store information within the server system 12 as well as interact with and operate the server system 12.

Referring again to FIG. 1, the third party computer servers 16 include information and data associated with medications. For example, in one embodiment, the third party computer servers 16 may include, for a particular medication, a name, drug class, shape, color, and imprint of the pill, strength, and typical dosage instructions. It may additionally include information about side effects and drug interactions.

In the illustrated embodiment, the server system 12 includes a website hosting server 34, a pharmacy account server 36, a search engine server 38, a database server 40, and a database 42. The database server 42 includes a memory device that is connected to the database 42 to retrieve and store information contained in the database 42. The database 42 contains information on a variety of matters, such as, for example, webpages associated with one or more websites, search queries, prescription drug information, over-the-counter (OTC) drug information, customer pharmacy account information, product records, notification messages, mobile device application program interfaces (APIs), and/or any suitable information that enables the system 10 to function as described herein.

Figure 3:
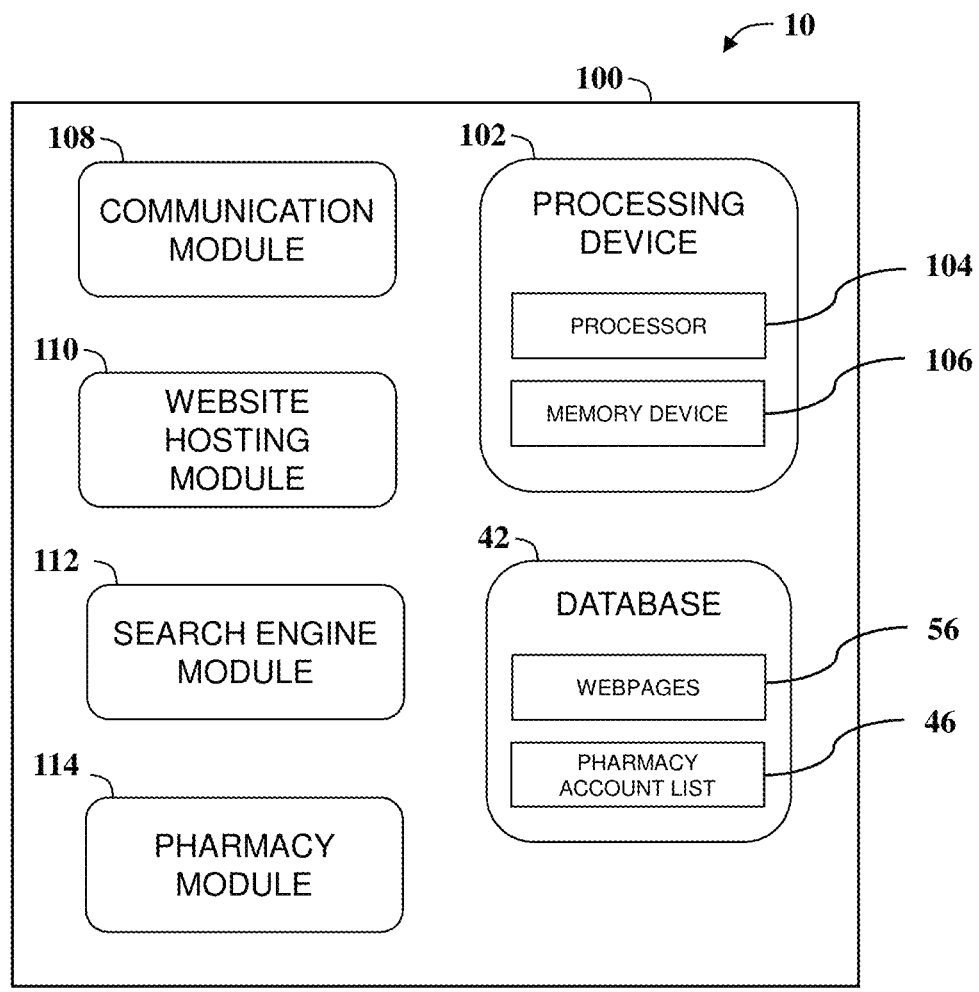
FIG. 3 is a schematic illustrating example components of a server computer that may be used with the system shown in FIG. 1, according to an embodiment of the present invention.

Referring now to FIG. 3, in one embodiment, the system 10 may include a system server 100 that is configured to perform the functions of the website hosting server 34, the pharmacy account server 36, the search engine server 38, and the database server 40. In the illustrated embodiment, the system server 100 includes a processing device 102 and the database 42.

The processing device 102 executes various programs, and thereby controls components of the system server 100 according to user instructions received from the user computing device 14. The processing device 102 may include memory device 106, e.g., read only memory (ROM) and random access memory (RAM), storing processor-executable instructions and one or more processors that execute the processor-executable instructions. The memory device 106 may include, but is not limited to, a hard disc drive, an optical disc drive, and/or a flash memory drive. Further, the memory device 106 may be distributed and located at multiple locations.

In embodiments where the processing device 102 includes two or more processors 104, the processors can operate in a parallel or distributed manner. In an example, the processing device 104 may execute a communications module 108, a website hosting module 110, a search engine module 112, and a pharmacy account module 114.

The communications module 108 retrieves various data and information from the database 42 and sends information to the user computing device 14 via the communications network 18 to enable the user to access and interact with the system 10. In one embodiment, the communications module 108 displays various images on a graphical interface of the user computing device 14 preferably by using computer graphics and image data stored in the database 42 including, but not limited to, web pages, pharmacy records, pharmacy notification messages, product lists, and/or any suitable information and/or images that enable the system 10 to function as described herein.

The website hosting module 110 may be programmed to perform some or all of the functions of the website hosting server 34 including hosting various web pages associated with one or more websites that are stored in the database 42 and that are accessible to the user via the user computing device 14. The website hosting module 110 may be programmed to generate and display web pages associated with a website in response to requests being received from users via corresponding web browsers.

The search engine module 112 may be programmed to perform some or all of the functions of the search engine server 38 including generating and storing search data in response to the user's search request and/or pharmacy account module 114 search requests.

The pharmacy account module 114 may be programmed to perform some or all of the functions of the pharmacy account server 36 including monitoring activities associated with pharmacy customers including new prescription and/or prescription refill requests and generate notification messages associated with the monitored activities. In addition, the pharmacy account module 114 may be programmed to perform calendared tasks requested by the user.

Referring now to FIG. 4, in one embodiment, the database 42 may contain a pharmacy account list 46 that includes a plurality of user pharmacy account records 48. Each user pharmacy account record 48 is associated with a corresponding pharmacy customer and includes user identification information 50 associated with the pharmacy customer and pharmaceutical drug information 52 associated with pharmaceutical drugs prescribed to and/or purchased by the corresponding pharmacy customer. The user identification information 50 includes user identifying data such as, for example, a unique ID and/or password. The user identification information 50 may also include user contact information such as, for example, a phone number, an email, and/or a mobile device data associated with a mobile computing device 20 associated with the corresponding pharmacy customer. For example, the mobile device data may include, but is not limited to, a unique mobile device ID, operating system, phone number, IP address, mobile device API, and/or any suitable information that enables the system 10 to communicate with the corresponding mobile computing device 20. The pharmaceutical drug information 52 includes information associated with a corresponding pharmaceutical drug such as, for example, a unique drug ID associated with the pharmaceutical drug, a drug name, drug category, prescribed use information, dosage, number of refills, side effects, and/or any relevant information associated with the corresponding pharmaceutical drug.

Figure 5:
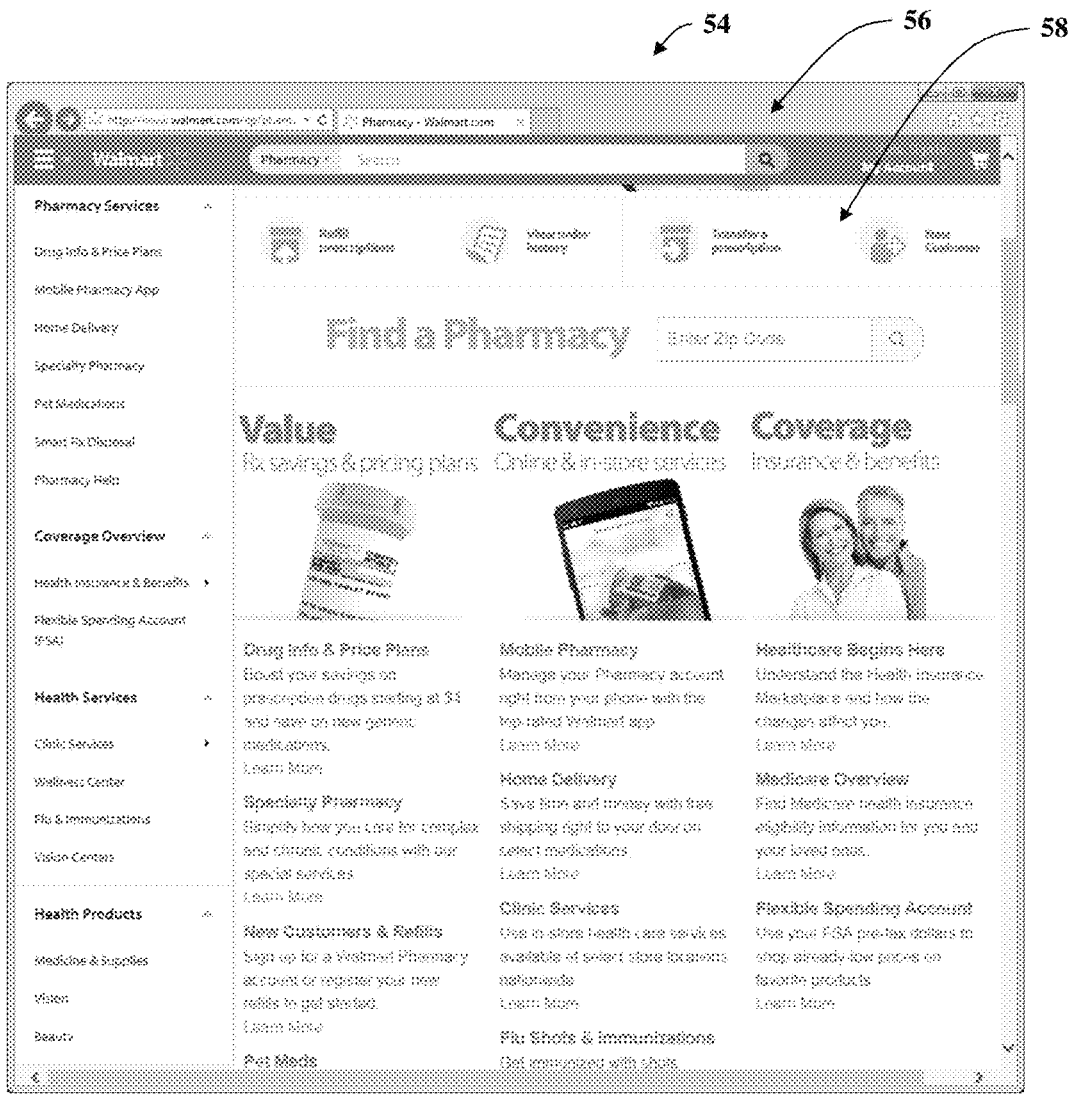
FIGS. 5-10 are illustrations of exemplary screenshots from the system of FIG. 1, according to an embodiment of the present invention.

Referring now to FIG. 5, the website hosting server 34 is configured to host a website 54 that is accessible by a user via one or more user computing devices 14. The website hosting server 34 retrieves and stores web pages 56 associated with one or more websites 54 in response to requests received by the user via the user computing device 14 to allow users to interact with the website and search and/or purchase products such as, for example, goods and/or services via the website. In one embodiment, the website hosting server 34 is configured to generate and display web pages 56 associated with the website in response to requests being received from consumers via corresponding web browsers that are displayed on the user computing devices 14.

Figure 6A:
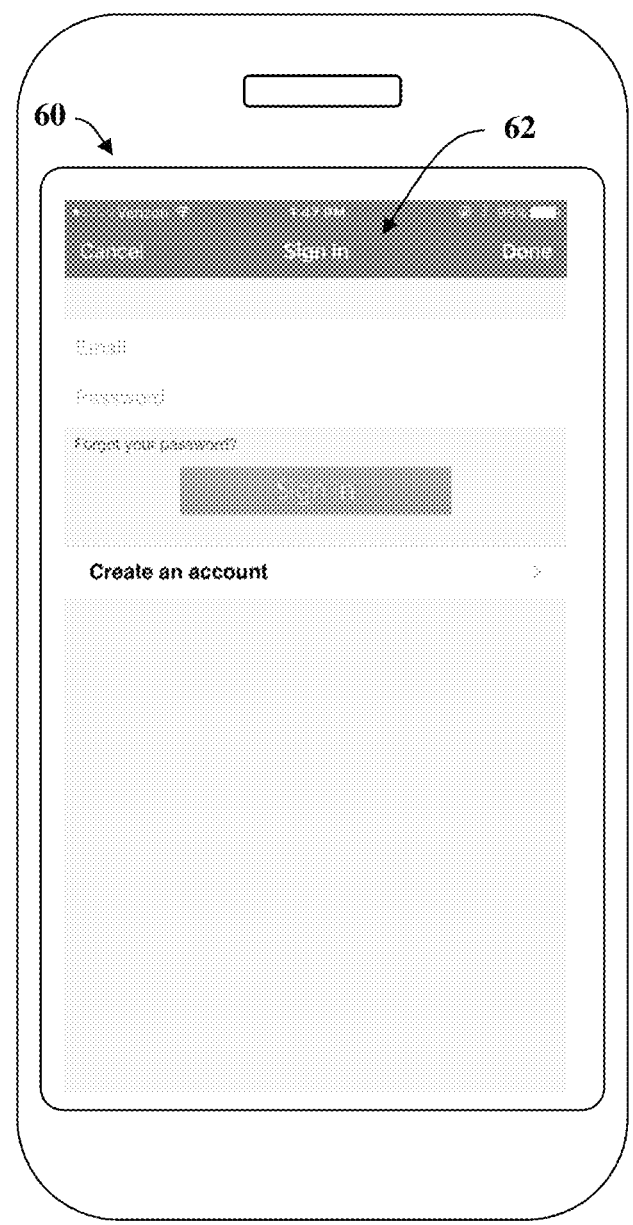
Figure 6B:
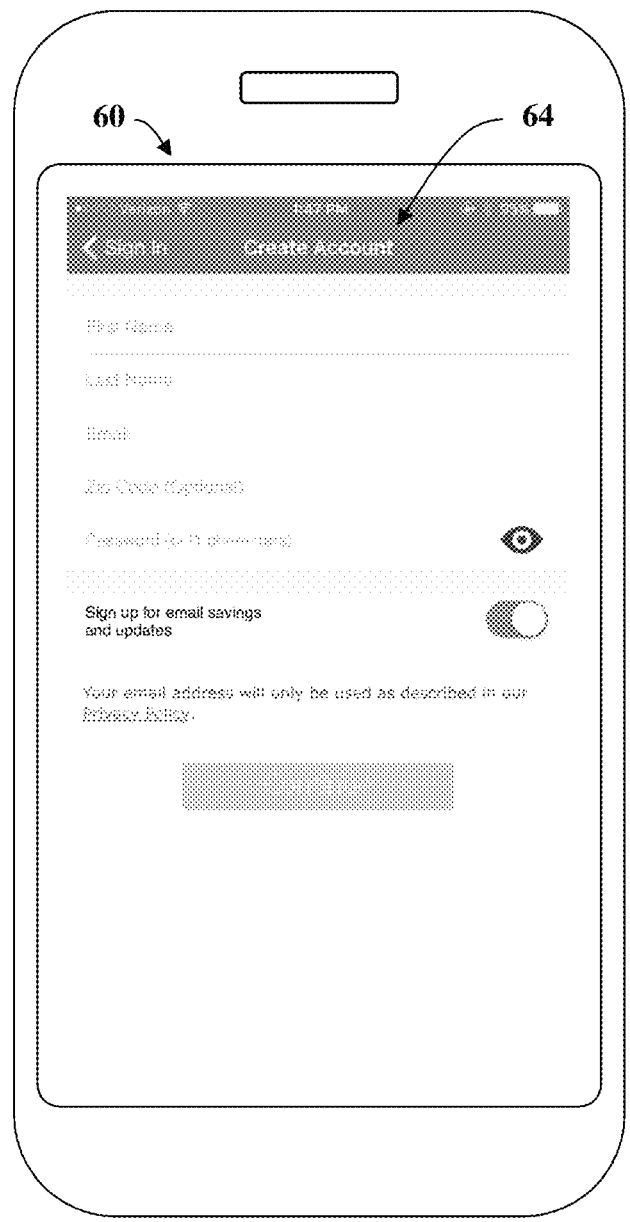

Referring now to FIGS. 6A and 6B, the website hosting server 34 may be configured to generate and display a mobile webpage 60 that is displayed on one or more mobile computing devices 20. For example, in one embodiment, the website hosting server 34 may display a mobile webpage 60 in response to receiving a user request that allows a user to access a corresponding customer pharmacy account record 48. In one embodiment, the website hosting server 34 may allow customers to login and access corresponding customer pharmacy accounts including account information such as, for example, previous purchases, pending prescription orders, pending prescription refills, and/or pharmaceutical drug information. For example, the website hosting server 34 may display a login page 62 for returning customers or create account page 64 for new customers, receive a unique customer ID such as, for example, a username and/or password, and identify the customer account associated with the unique customer ID to enable the identified customer to access information and/or features associated with the corresponding customer pharmacy account.

Referring again to FIG. 1, the pharmacy account server 36 is programmed to monitor activities associated with prescription drugs being used by pharmacy customers. In addition, the pharmacy account server 36 is programmed to detect the occurrence of triggering events associated with pharmaceutical drugs being used by pharmacy customers and transmit pharmacy notification messages to the customers to assist the customers with medication adherence.

In one embodiment, the pharmacy account server 36 may determine the triggering event to include an indication of a new prescription or a refilled prescription through the mobile webpage 60. The pharmacy account server 36 may be programmed to receive a signal indicating a new or updated pharmaceutical drug associated with a pharmacy customer. The signal may include an indication of a new prescription and/or include a request to fill a prescription received from the mobile webpage 60. In addition, the signal may include a pharmaceutical drug ID and a user ID. In one embodiment, the pharmacy account server 36 may access the pharmacy account list 46 being stored in the database an determine the user pharmacy account records 48 that is associated with the received user ID, determine one or more pharmaceutical drugs associated with the user ID, and determine the pharmaceutical drug ID associated with each corresponding pharmaceutical drug.

Figure 7:
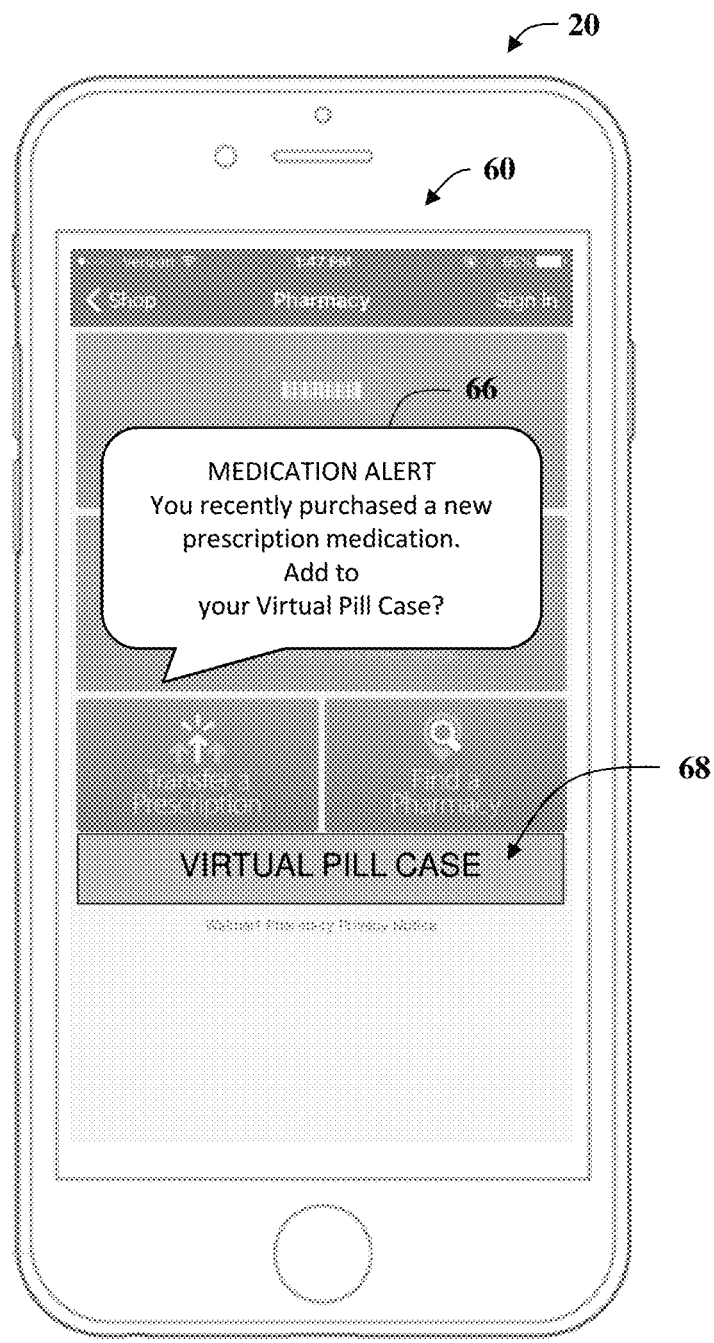

The pharmacy account server 36 may be alerted of the new prescription or new refill by a point-of-sale transaction associated with the user ID. Referring now to FIG. 7, the pharmacy account server 36 generates a pharmacy notification message 66 requesting that the pharmacy customer add the new prescription or new refill information to the pharmacy customer's virtual pill case 68. The pharmacy account server 36 then generates and transmits a signal including the pharmacy notification message to the mobile computing device 20 to cause the mobile computing device 20 to display the pharmacy notification message on the mobile computing device 20.

Figure 8:
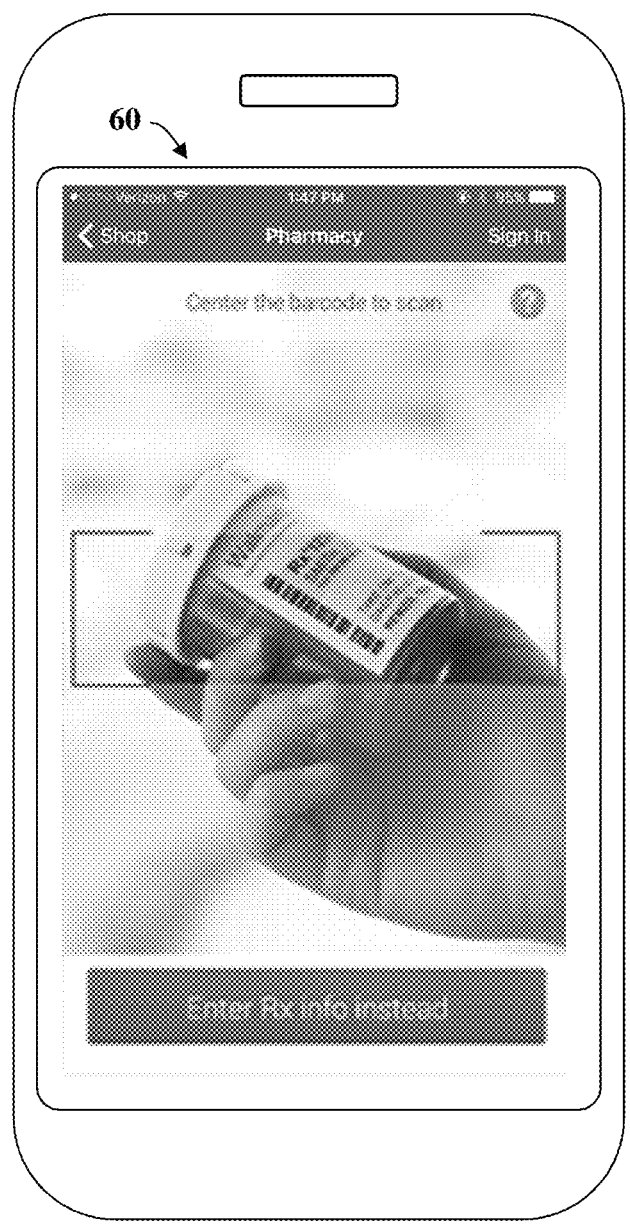

Referring now to FIG. 8, alternatively, the pharmacy customer may indicate the new prescription or new refill to the pharmacy account server 36, which may prompt the user to input the prescription information (e.g., by scanning a barcode associated with the prescription or by manually entering prescription information) via mobile webpage 60.

In one embodiment, the system 10 may periodically prompt the pharmacy customer to transfer any prescriptions that may be administered by other pharmacies to the pharmacy associated with the virtual pill case.

In one embodiment, once the new prescription or new refill information has been received by the pharmacy account server 36, the pharmacy account server 36 may initiate a data search operation including transmitting the prescription information to the search engine server 38. In one embodiment, during the data search operation, the pharmacy account server 36 generates search terms associated with a prescribed pharmaceutical drug included in the identified user pharmacy account record 48 and transmits the search terms to the search engine server 38. The search engine server 38 may initiate a search on the third party computer server 16. The search results may be transmitted from the search engine server 38 to the pharmacy account server 36. The search results may include information about the pharmaceutical drug, including information about the pill shape, size, color, and strength, and an image or photograph representing the pill (or inhaler, pump, patch, or other device by which the pharmaceutical drug is administered).

The pharmacy account server 36 may receive the search results from the search engine module 38 and evaluate the search results to retrieve new or updated information associated with the pharmaceutical drug.

Figure 9A:
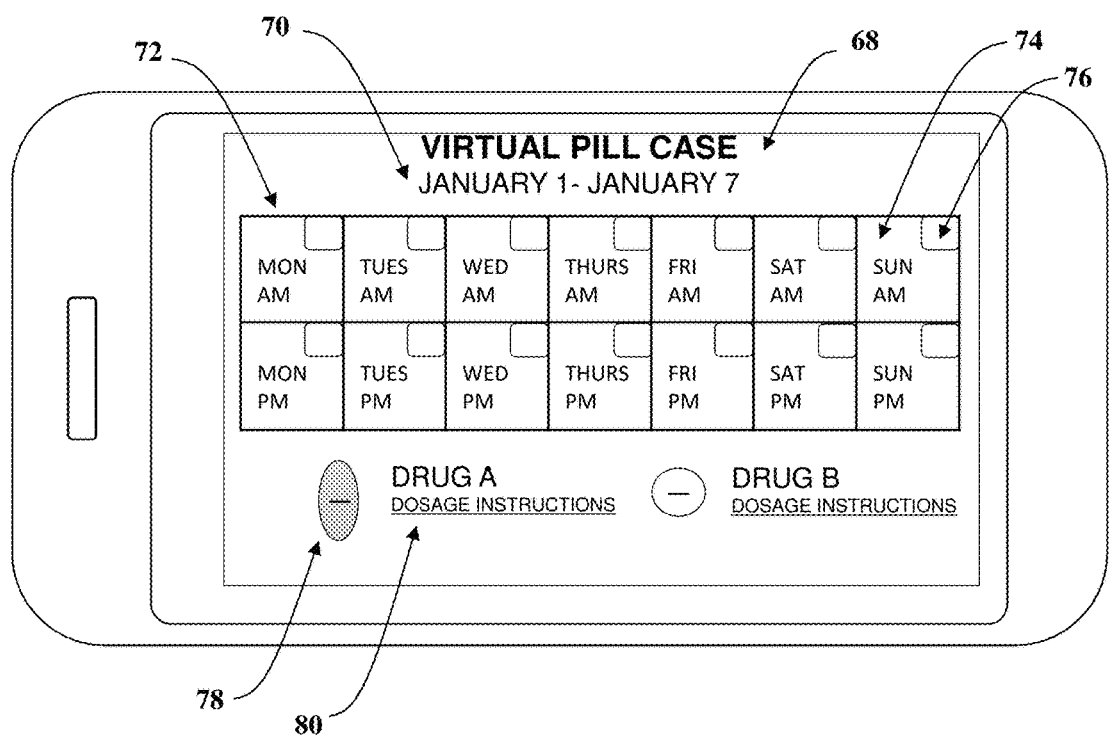

Referring now to FIG. 9A, the pharmacy account server 36 may store the retrieved information about the prescribed pharmaceutical drug and the prescription information in a virtual pill case 68 associated with the pharmacy customer. The virtual pill case 68 may display a date range 70. The date range 70 may correspond to a calendar 72, which may have a separate entry 74 for each day of the week and, in some cases, entries for different times of day (e.g., AM and PM), similar to a traditional physical pill case. Each entry 74 may have a checkbox 76 to indicate whether the pharmacy customer has taken the prescribed dose for that day and/or time. An image 78 showing the pill associated with the pharmaceutical drug may also be displayed, along with a hyperlink 80 to additional information about the pharmaceutical drug including dosage instructions. All currently prescribed pharmaceutical drugs stored in database 42 and associated with the customer ID of the pharmacy customer will be shown in the virtual pill case 68 (e.g., DRUG A and DRUG B).

Figure 9B:
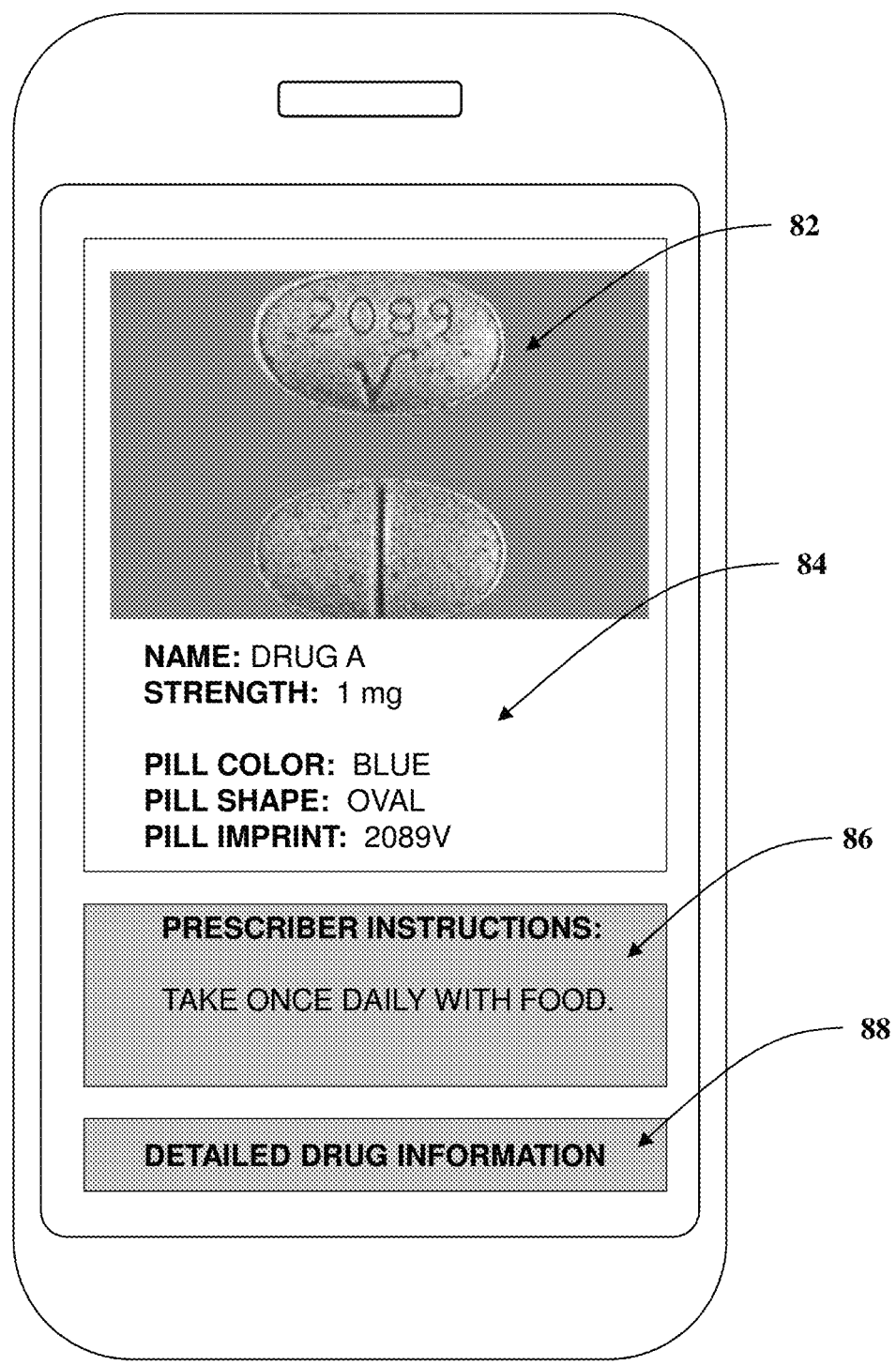

Referring now to FIG. 9B, when the pharmacy customer follows hyperlink 80 from FIG. 7, the additional information about the pharmaceutical drug is displayed. In the illustrated embodiment, a photograph 82 shows the pill (or other medication administration device) associated with the pharmaceutical drug. Drug details 84 include, for example, the name, class, and strength of the drug, as well as the shape, color, and imprint of the pill. Additionally, dosage instructions 86 are displayed, which include personalized instructions for administration of the medication as prescribed for the pharmacy customer. The pharmacy customer may access additional information via a hyperlink 88, which may take the pharmacy customer to a third party website and display, for instance, information about side effects and drug and food interactions associated with the pharmaceutical drug.

Figure 9C:
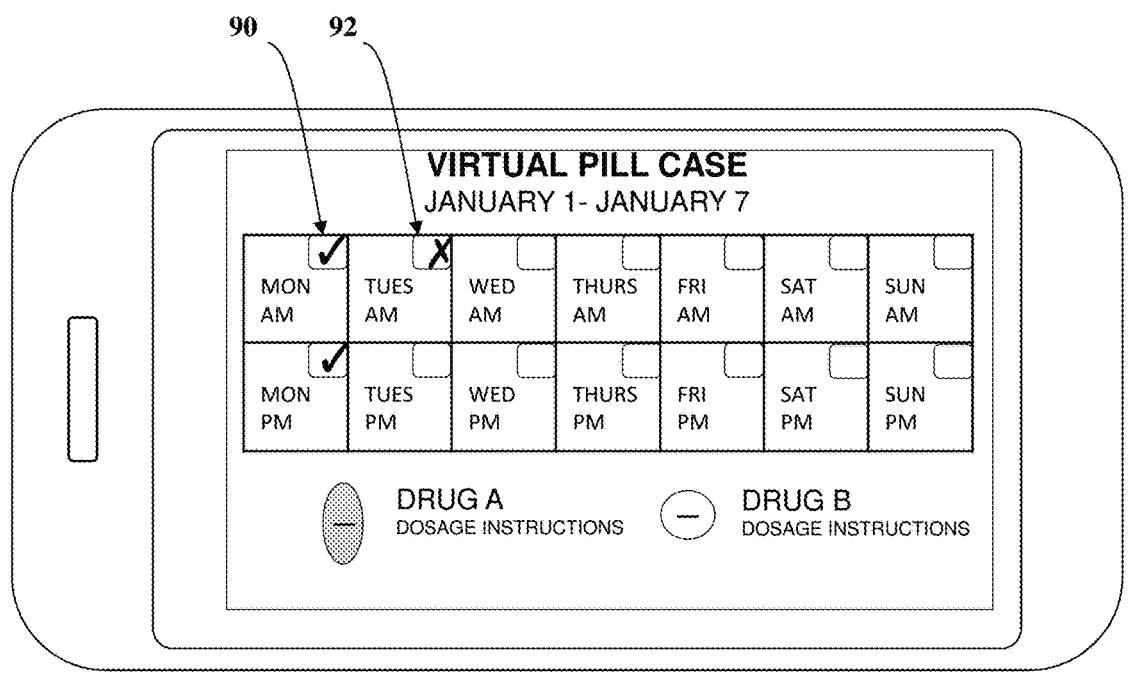

Referring now to FIG. 9C, the pharmacy customer may indicate that a dosage was taken by placing a taken dose symbol 90. If the pharmacy customer misses a dose, a missed dose symbol 92 may be shown. In response to a missed dose, a pharmacy notification may be sent to the pharmacy customer.

Figure 10:
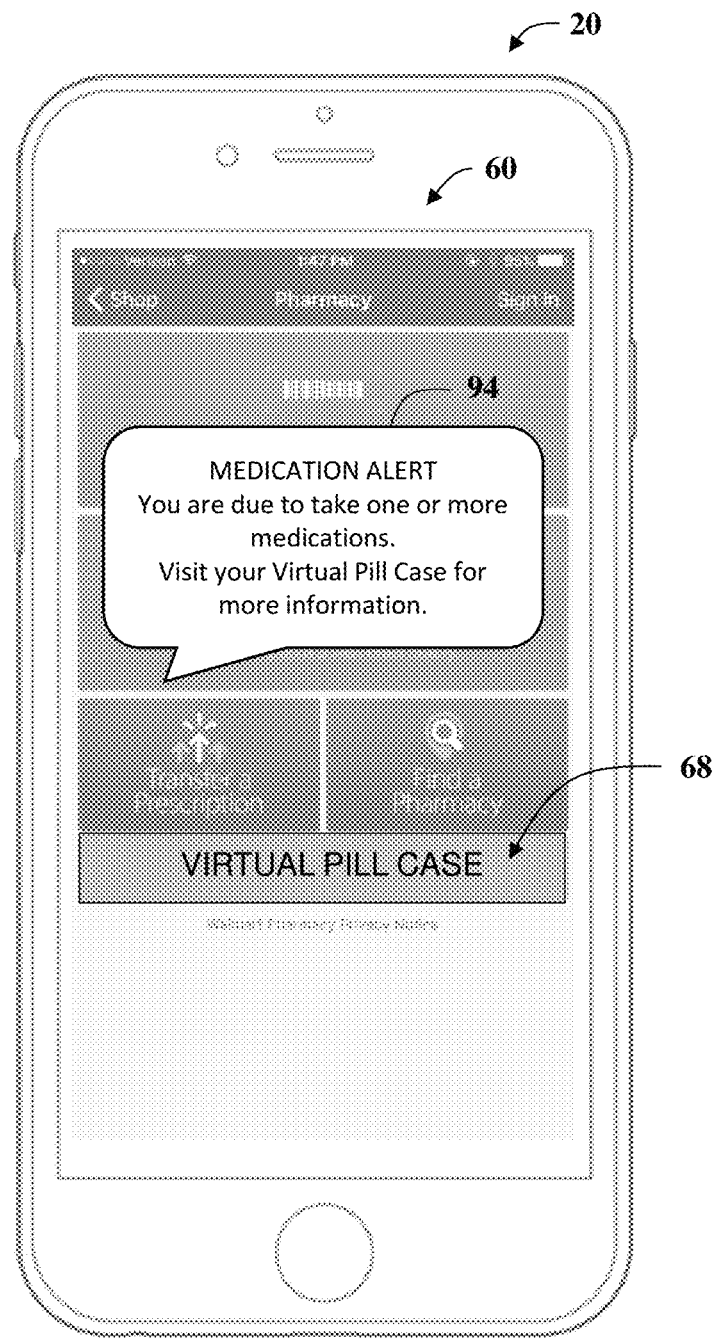

Referring now to FIG. 10, in one embodiment, the pharmacy account server 36 may receive a request to display a pharmacy notification message 94 to the pharmacy customer via a user computing device 14. In one embodiment, the pharmacy account server 36 may receive a request to display the pharmacy notification message on a mobile computing device 20. The request may include a corresponding user ID. Upon receiving the request, the pharmacy account server 36 accesses the database 42 and identifies a user pharmacy account record 48 associated with the received user ID. The pharmacy account server 36 detects an occurrence of a triggering event as a function of the triggering event data, such as a missed dose by the pharmacy customer, and generates the pharmacy notification message 94. The pharmacy account server 36 then generates and transmits a signal including the pharmacy notification message to the mobile computing device 20 to cause the mobile computing device 20 to display the pharmacy notification message on the mobile computing device 20.

FIGS. 11-14 are flowcharts of methods 200, 300, 400, and 500 that may be used with the system 10 for monitoring activities of pharmacy customers and generating and displaying information to the pharmacy customers on a website via a mobile computing device. The methods include a plurality of steps. Each method step may be performed independently of, or in combination with, other method steps. Portions of the methods may be performed by any one of, or any combination of, the components of the system 10.

Figure 11:
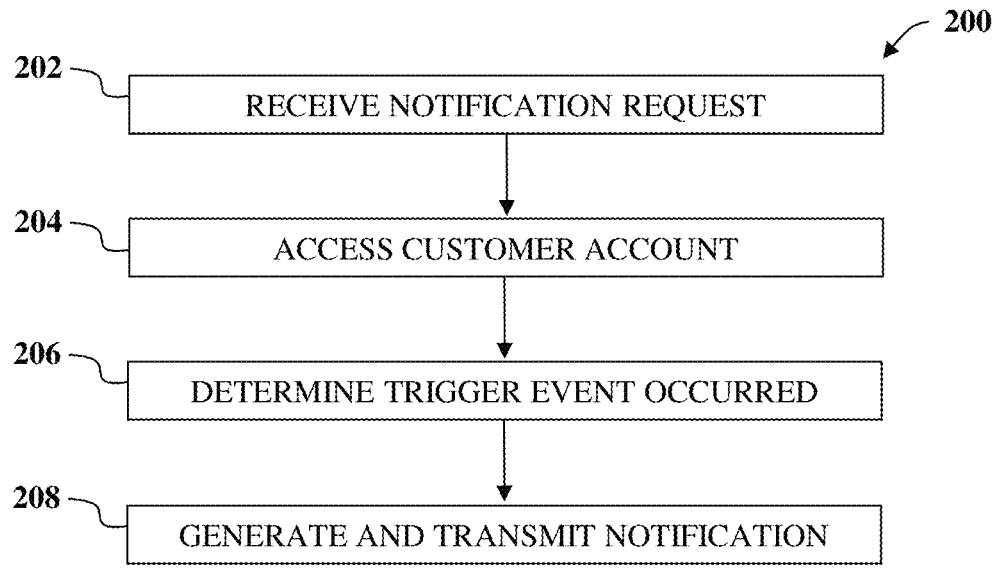
FIGS. 11-14 are flowcharts of methods that may be used with the system shown in FIG. 1, according to embodiments of the present invention.

Referring now to FIG. 11, a method 200 for determining new prescription information is available is shown. At step 202, the pharmacy account server 36 receives a request to initiate a notification operation to monitor an activity of a pharmacy customer. The request includes a corresponding user ID. In one embodiment, the request may be received from a mobile computing device 20 associated with a pharmacy customer. In another embodiment, the request may be initiated by the customer via the pharmacy website. In addition, the pharmacy account server 36 may be programmed to initiate a notification operation at a specific time and/or upon receiving an indication of activities associated with a pharmacy customer.

At step 204, the pharmacy account server 36 accesses the user pharmacy account list 46 being stored in the database 42 to determine a user pharmacy account records 48 associated with the received user ID.

At step 206, the pharmacy account server 36 determines that a triggering event has occurred. For example, in one embodiment, the triggering event may include a purchase of a new prescription by the pharmacy customer associated with the user ID. In another embodiment, the triggering event may include an indication that a pharmaceutical drug associated with the user ID requires a refill.

At step 208, the pharmacy account server 36 generates and transmits a pharmacy notification message to the pharmacy customer requesting that the pharmacy customer add the new prescription information to the pharmacy customer's virtual pill case 68. In the illustrated embodiment, the pharmacy account server 36 generates and transmits a signal including the notification message to the mobile computing device 20 to cause the mobile computing device 20 to display the notification message on the mobile computing device 20. For example, the pharmacy account server 36 may generate a notification 66 (shown in FIG. 7) upon detecting a new prescription or new refill. In one embodiment, the system 10 may access the corresponding user pharmacy account records 48 to determine a messaging API associated with an operating system of the mobile computing device 20 and generate the notification message as a function of the retrieved messaging API to enable the mobile computing device 20 to display the received message. In one embodiment, each user account record includes information associated with the mobile computing device 20 including a unique mobile ID and message API. In another embodiment, the user pharmacy account records 48 may include a message preferences, such as, for example, an email, text message, push messaging, automated phone call, and the like. The pharmacy account server 36 identifies the messaging preference associated with the user pharmacy account records 48 and generates the notification message based on the message preference.

Figure 12:
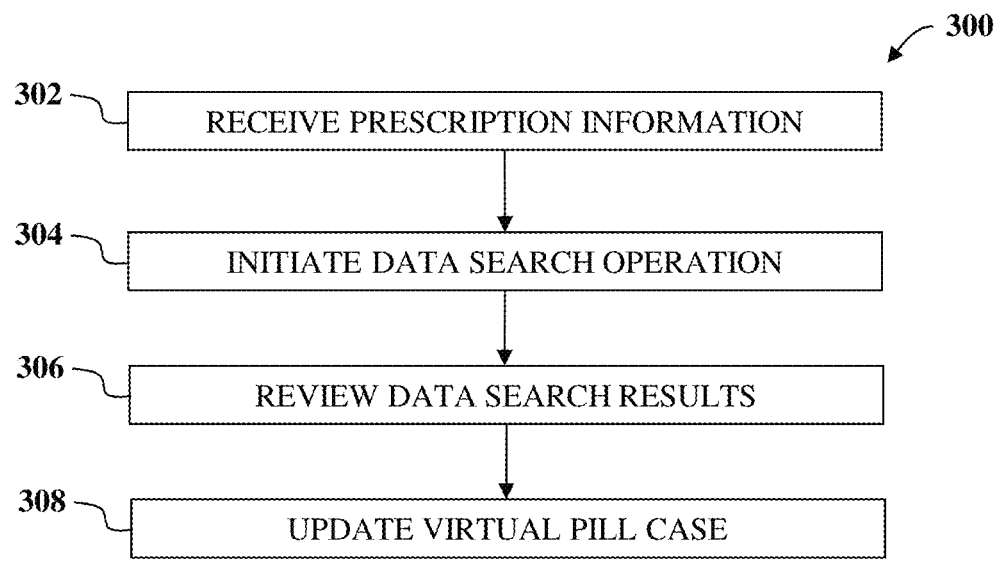

Referring now to FIG. 12, a method 300 for acquiring new prescription information is shown. At step 302, prescription information is received (e.g., manually entered by the pharmacy customer or received via an electronic transaction record).

At step 304, the pharmacy account server 36 initiates a data search operation including transmitting the prescription information to the search engine server 38. In one embodiment, during the data search operation, the pharmacy account server 36 generates search terms associated with a prescribed pharmaceutical drug included in the identified user pharmacy account record 48 and transmits the search terms to the search engine server 38. The search engine server 38 may initiate a search on the third party computer server 16. The search results may be transmitted from the search engine server 38 to the pharmacy account server 36. The search results may include information about the pharmaceutical drug, including information about the pill shape, size, color, and strength, and an image or photograph representing the pill (or inhaler, pump, patch, or other device by which the pharmaceutical drug is administered).

At step 306, the pharmacy account server 36 reviews the data search results and determines whether new information not already stored in the virtual pill case has been retrieved. For example, the prescription information may correspond to a refill of a pharmaceutical drug that is already stored in the pharmacy customer's virtual pill case, but the search results may indicate new information is available for the pharmaceutical drug because the manufacturer has changed the pill shape since the pharmacy customer's previous refill.

At step 308, the virtual pill case is updated with any new information retrieved via the search results.

Figure 13:
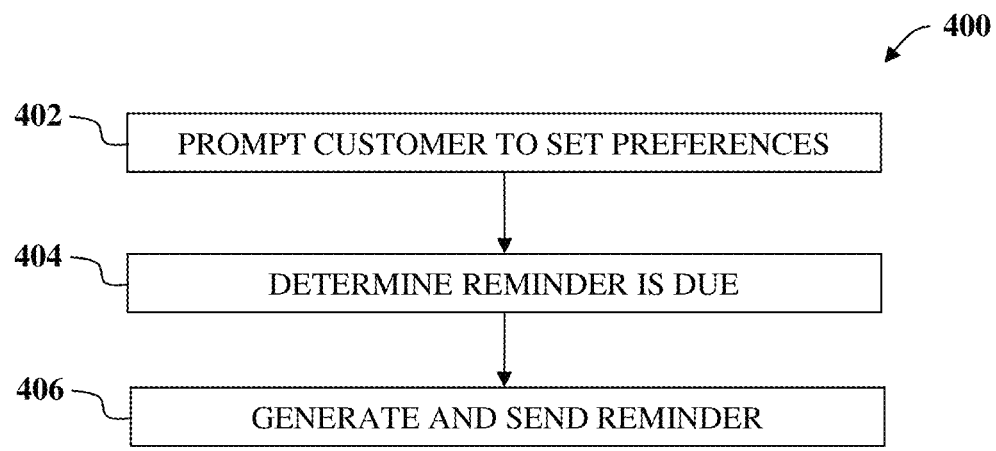

Referring now to FIG. 13, a method 400 for sending a reminder to pharmacy customer regarding a virtual pill case. At step 402, the pharmacy account server 36 prompts a pharmacy customer to set one or more reminder preferences regarding a virtual pill case. Reminder preferences may include, for example, whether the customer wishes to receive reminders regarding the virtual pill case. If the customer wishes to receive reminders, the customer may indicate a frequency with which the reminder should be sent (e.g., daily, weekly, etc.) and when the reminder should be sent (e.g., in the morning, afternoon, or evening, or at a specific time). The user may also indicate whether the reminder should be sent only if the user has missed a scheduled medication dose, or if the reminder should always be sent. Additionally, the user may indicate the preferred method of transmission of the reminder (e.g., push notification, text message, e-mail, etc.).

At step 404, the pharmacy account server 36 determines that a reminder to the pharmacy customer is due, based on the customer's set reminder preferences. At step 406, the pharmacy account server 36 generates and sends a reminder to the pharmacy customer regarding the virtual pill case.

Figure 14:
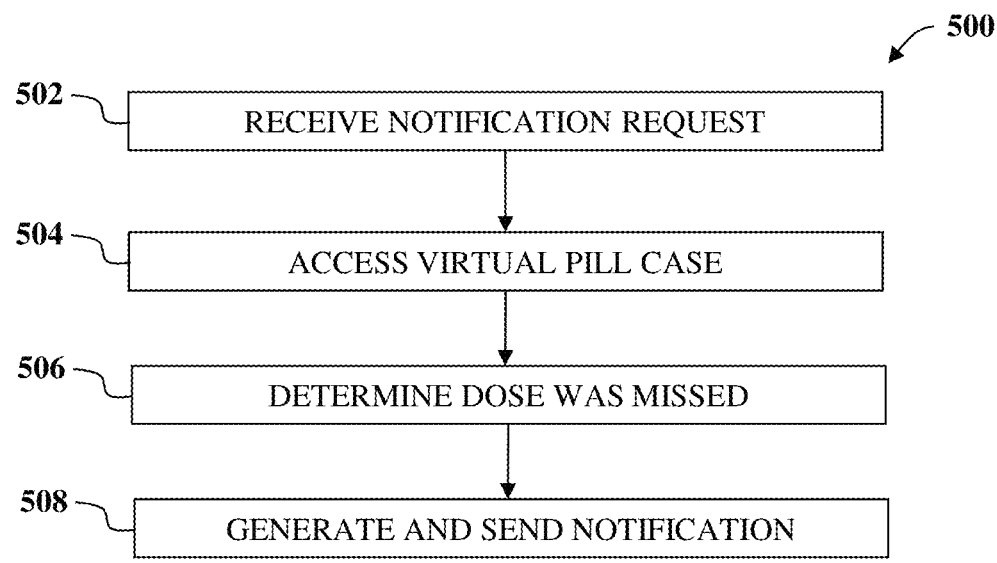

Referring now to FIG. 14, a method 500 for sending a missed dose notification to pharmacy customer using a virtual pill case. At step 502, the pharmacy account server 36 receives a request to initiate a notification operation to monitor an activity of a pharmacy customer. The request includes a corresponding user ID. In one embodiment, the request may be received from a mobile computing device 20 associated with a pharmacy customer. In another embodiment, the request may be initiated by the customer via the pharmacy website. In addition, the pharmacy account server 36 may be programmed to initiate a notification operation at a specific time and/or upon receiving an indication of activities associated with a pharmacy customer.

At step 504, the pharmacy account server 36 accesses a virtual pill case associated with the pharmacy customer. At step 506, the pharmacy account server 36 determines that the pharmacy customer missed at least one scheduled dose of a pharmaceutical drug according to dosage instructions provided by a prescriber. At step 508, the pharmacy account server 36 generates and sends a notification to the pharmacy customer regarding the missed dose and prompting the user to visit the virtual pill case to review dosage instructions.

A controller, computing device, server or computer, such as described herein, includes at least one or more processors or processing units and a system memory (see above). The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor.

In some embodiments, a database, as described herein, includes any collection of data including hierarchical databases, relational databases, flat file databases, object-relational databases, object oriented databases, and any other structured collection of records or data that is stored in a computer system. The above examples are exemplary only, and thus are not intended to limit in any way the definition and/or meaning of the term database. Examples of databases include, but are not limited to only including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

Other features of the system 10 can be found in the following commonly owned U.S. Patent Applications, which are hereby incorporated by reference: U.S. patent application Ser. No. 15/009,327, filed on Jan. 28, 2016; U.S. patent application Ser. No. 15/009,417, filed on Jan. 28, 2016; U.S. patent application Ser. No. 15/009,561, filed on Jan. 28, 2016; U.S. patent application Ser. No. 15/009,436, filed on Jan. 28, 2016; U.S. patent application Ser. No. 15/009,654, filed on Jan. 28, 2016; U.S. patent application Ser. No. 15/009,583, filed on Jan. 28, 2016; U.S. patent application Ser. No. 15/009,454, filed on Jan. 28, 2016; U.S. patent application Ser. No. 15/009,598, filed on Jan. 28, 2016; U.S. patent application Ser. No. 15/009,611, filed on Jan. 28, 2016; U.S. patent application Ser. No. 15/009,634, filed on Jan. 28, 2016; and, U.S. patent application Ser. No. 15/009,644, filed on Jan. 28, 2016.

The above description of illustrated examples of the present invention, including what is described in the Abstract, are not intended to be exhaustive or to be limitation to the precise forms disclosed. While specific embodiments of, and examples for, the invention are described herein for illustrative purposes, various equivalent modifications are possible without departing from the broader spirit and scope of the present invention.

What is claimed is:

1. A system comprising:
   a first user interface on a user device accessible to a user and including a virtual pill case, the virtual pill case comprising:
      a date range;
      first prescription information about at least one medication, wherein:
         the first prescription information comprises dosage instructions for the at least one medication; and
         the at least one medication is scheduled to be taken by the user during the date range;
      a first image of the at least one medication;
      a first customized hyperlink; and
      a selectable user interface element corresponding to the at least one medication;
   a second user interface on the user device accessible to the user when the user selects the first customized hyperlink, the second user interface comprising:
      a second image of the at least one medication, the second image of the at least one medication being larger than the first image of the at least one medication;
      second prescription information about the at least one medication, the second prescription information comprising:
         a name of the at least one medication;
         a class of the at least one medication;
         a dosage strength of the at least one medication;
         a shape of the at least one medication;
         a color of the at least one medication; and
         an imprint of the at least one medication; and
      a second customized hyperlink configured to navigate a web browser on the user device to a third-party website comprising side effect information about the at least one medication and adverse interaction information about the at least one medication; and
   a processing device in communication with the first user interface or the second user interface, the processing device comprising:

a pharmacy account module configured to:
  receive a request to initiate a notification operation to monitor an activity of the user, the activity corresponding to a use of the at least one medication;
  store the request to initiate the notification operation in a database; and
  initiate a data search operation including transmitting the first prescription information to a search engine module;
the search engine module configured to:
  receive the first prescription information from the pharmacy account module;
  in response to receiving the first prescription information, automatically generate a request to search the first prescription information on a third party server;
  receive search results associated with the first prescription information from the third party server; and
  in response to receiving the search results, automatically send the search results to the pharmacy account module;
the pharmacy account module further configured to:
  receive the search results from the search engine module;
  in response to receiving the search results, automatically evaluate the search results to retrieve updated information associated with the at least one medication;
  update the at least one medication in the virtual pill case with the updated information;
  determine that a triggering event has occurred, wherein the triggering event is associated with the at least one medication; and
  in response to determining that the triggering event has occurred, automatically generate a notification regarding the triggering event;
a communications module configured to:
  transmit the notification to the user; and
  receive, from the user, a selection of the selectable user interface element corresponding to the at least one medication, the selection of the selectable user interface element indicating a use of the at least one medication by the user;
  transmit the selection of the selectable user interface element to the pharmacy account module;
  receive a selection of the first customized hyperlink; and
  transmit the second user interface to a customer control unit; and
the pharmacy account module further configured to:
  receive the selection from the communications module; and
  in response to receiving the selection, resolve the triggering event.

2. The system of claim 1, wherein the request to initiate the notification operation includes one or more user preferences.

3. The system of claim 2, wherein the one or more user preferences include a preferred notification frequency.

4. The system of claim 2, wherein the one or more user preferences include a preferred method of notification transmission.

5. The system of claim 2, wherein the one or more user preferences include a preferred time of day for notification transmission.

6. The system of claim 1, wherein the communications module is further configured to prompt the user to access the virtual pill case.

7. The system of claim 6, wherein the communications module is further configured to prompt the user to view the dosage instructions associated with the at least one medication.

8. A computer-implemented method comprising:
  receiving, by a pharmacy account module of a server, a request to initiate a notification operation to monitor an activity of a user, the activity corresponding to a use of at least one medication;
  storing, in a database on the server, the request to initiate the notification operation;
  initiating, by the pharmacy account module, a data search operation including transmitting prescription information to a search engine module;
  receiving, by the search engine module from the pharmacy account module, the prescription information;
  in response to receiving the prescription information, automatically generating, by the search engine module, a request to search the prescription information on a third party server;
  receiving, by the search engine module, search results associated with the prescription information from the third party server;
  in response to receiving the search results, automatically sending, by the search engine module, the search results to the pharmacy account module;
  receiving, by the pharmacy account module, the search results from the search engine module;
  in response to receiving the search results, automatically evaluating, by the pharmacy account module, the search results in order to retrieve updated information associated with the at least one medication;
  updating, by the pharmacy account module, first prescription information about the at least one medication displayed in a virtual pill case on a first user interface of a customer control unit using the updated information associated with the at least one medication, the virtual pill case comprising:
    a date range;
    the first prescription information about the at least one medication, wherein:
      the first prescription information comprises dosage instructions for the at least one medication; and
      the at least one medication is scheduled to be taken by the user during the date range;
    a first image of the at least one medication;
    a first customized hyperlink; and
    a selectable user interface element corresponding to the at least one medication;
  determining, by the pharmacy account module, that a triggering event has occurred, wherein the triggering event is associated with the at least one medication;
  in response to determining that the triggering event has occurred, automatically generating, by the pharmacy account module, a notification regarding the triggering event;
  transmitting, by a communications module, the notification to the user
  receiving, by the communications module from the user, a selection of the selectable user interface element corresponding to the at least one medication, the selection indicating a use of the at least one medication by the user;

transmitting, by the communications module, the selection of the selectable user interface element to the pharmacy account module;

receiving, by the pharmacy account module from the communications module, the selection of the selectable user interface element from the communications module;

in response to receiving the selection of the selectable user interface element, resolving, by the pharmacy account module, the triggering event;

receiving, by the communications module, a selection of the first customized hyperlink; and transmitting, by the communications module, a second user interface to the customer control unit, the second user interface comprising:
   a second image of the at least one medication, the second image of the at least one medication being larger than the first image of the at least one medication;
   second prescription information about the at least one medication, the second prescription information comprising:
      a name of the at least one medication;
      a class of the at least one medication;
      a dosage strength of the at least one medication;
      a shape of the at least one medication;
      a color of the at least one medication; and
      an imprint of the at least one medication; and
   a second customized hyperlink configured to navigate a web browser on a user device to a third-party website comprising side effect information about the at least one medication and adverse interaction information about the at least one medication.

9. The method of claim 8, wherein the request to initiate the notification operation includes one or more user preferences.

10. The method of claim 9, wherein the one or more user preferences include a preferred notification frequency.

11. The method of claim 9, wherein the one or more user preferences include a preferred method of notification transmission.

12. The method of claim 9, wherein the one or more user preferences include a preferred time of day for the notification transmission.

13. The method of claim 8, wherein the communications module is further configured to prompt the user to access the virtual pill case.

14. The method of claim 13, wherein the communications module is further configured to prompt the user to view the dosage instructions associated with the at least one medication.

15. A non-transitory information recording medium on which a computer readable program is recorded that causes a computer to function as a system comprising:
   a first user interface on a user device accessible to a user and including a virtual pill case, the virtual pill case comprising:
      a date range;
      first prescription information about at least one medication, wherein:
         the first prescription information comprises dosage instructions for the at least one medication; and
         the at least one medication is scheduled to be taken by the user during the date range;
      a first image of the at least one medication;
      a first customized hyperlink; and
      a selectable user interface element corresponding to the at least one medication;
   a second user interface on the user device accessible to the user when the user selects the first customized hyperlink, the second user interface comprising:
      a second image of the at least one medication, the second image of the at least one medication being larger than the first image of the at least one medication;
      second prescription information about the at least one medication, the second prescription information comprising:
         a name of the at least one medication;
         a class of the at least one medication;
         a dosage strength of the at least one medication;
         a shape of the at least one medication;
         a color of the at least one medication; and
         an imprint of the at least one medication; and
      a second customized hyperlink configured to navigate a web browser on the user device to a third-party website comprising side effect information about the at least one medication and adverse interaction information about the at least one medication; and
   a processing device in communication with the first user interface or the second user interface, the processing device comprising:
      a pharmacy account module configured to:
         receive a request to initiate a notification operation to monitor an activity of the user, the activity corresponding to a use of the at least one medication;
         store the request to initiate the notification operation in a database; and
         initiate a data search operation including transmitting the first prescription information to a search engine module;
      the search engine module configured to:
         receive the first prescription information from the pharmacy account module;
         in response to receiving the first prescription information, automatically generate a request to search the first prescription information on a third party server;
         receive search results associated with the first prescription information from the third party server; and
         in response to receiving the search results, automatically send the search results to the pharmacy account module;
      the pharmacy account module further configured to:
         receive the search results from the search engine module;
         in response to receiving the search results, automatically evaluate the search results to retrieve updated information associated with the at least one medication;
         update the at least one medication in the virtual pill case with the updated information;
         determine that a triggering event has occurred, wherein the triggering event is associated with the at least one medication; and
         in response to determining that the triggering event has occurred, automatically generate a notification regarding the triggering event;
      a communications module configured to:
         transmit the notification to the user; and
         receive, from the user, a selection of the selectable user interface element corresponding to the at least one medication, the selection of the selectable user interface element indicating a use of the at least one medication by the user;

transmit the selection of the selectable user interface element to the pharmacy account module;

receive a selection of the first customized hyperlink; and transmit the second user interface to a customer control unit and the pharmacy account module further configured to:

receive the selection from the communications module; and in response to receiving the selection, resolve the triggering event.

16. The non-transitory information recording medium of claim 15, wherein the request to initiate the notification operation includes one or more user preferences.

17. The non-transitory information recording medium of claim 16, wherein the one or more user preferences include a preferred notification frequency.

18. The non-transitory information recording medium of claim 16, wherein the one or more user preferences include a preferred method of notification transmission.

19. The non-transitory information recording medium of claim 16, wherein the one or more user preferences include a preferred time of day for the notification.

20. The non-transitory information recording medium of claim 15, wherein the communications module is further configured to prompt the user to access the virtual pill case.

21. The non-transitory information recording medium of claim 20, wherein the communications module is further configured to prompt the user to view the dosage instructions associated with the at least one medication.

* * * * *